United States Patent [19]
Komardin et al.

[11] Patent Number: 6,054,712
[45] Date of Patent: Apr. 25, 2000

[54] INSPECTION EQUIPMENT USING SMALL-ANGLE TOPOGRAPHY IN DETERMINING AN OBJECT'S INTERNAL STRUCTURE AND COMPOSITION

[75] Inventors: Oleg V. Komardin, Moscow, Russian Federation; Albert F. Lawrence, Escondida; Pavel I. Lazarev, Menlo Park, both of Calif.

[73] Assignee: Quanta Vision, Inc., San Mateo, Calif.

[21] Appl. No.: 09/012,771

[22] Filed: Jan. 23, 1998

[51] Int. Cl.[7] .................................................. G01N 23/04
[52] U.S. Cl. .................................. 250/363.06; 250/363.1
[58] Field of Search ........................... 250/363.06, 363.1; 378/88, 90

[56] References Cited

U.S. PATENT DOCUMENTS

| | | | |
|---|---|---|---|
| 4,549,307 | 10/1985 | Macovski | 378/145 |
| 4,651,002 | 3/1987 | Anno | 250/336.1 |
| 4,751,722 | 6/1988 | Harding et al. | 378/6 |
| 4,754,469 | 6/1988 | Harding et al. | 378/88 |
| 4,956,856 | 9/1990 | Harding | 378/88 |
| 5,007,072 | 4/1991 | Jenkins et al. | 378/88 |
| 5,008,911 | 4/1991 | Harding | 378/86 |
| 5,231,652 | 7/1993 | Harding | 378/88 |
| 5,265,144 | 11/1993 | Harding et al. | 378/86 |
| 5,394,453 | 2/1995 | Harding | 378/86 |
| 5,600,700 | 2/1997 | Krug et al. | 378/90 |

FOREIGN PATENT DOCUMENTS

| | | |
|---|---|---|
| 2012872 C1 | 5/1994 | Russian Federation . |
| 1402871 A1 | 6/1988 | U.S.S.R. . |
| 2299251 | 9/1996 | United Kingdom . |
| WO 96/17240 | 6/1996 | WIPO . |

Primary Examiner—Edward P. Westin
Assistant Examiner—Richard Hanig
Attorney, Agent, or Firm—Skjerven, Morrill, MacPherson, Franklin & Friel LLP; David T. Millers

[57] ABSTRACT

Devices for X-ray topography determine structures and compositions of objects. In accordance with an embodiment of the invention, a scanning system forms images using small angle scattering. A spatial filter selects radiation an object scatters at small angles and blocks other radiation. A coordinate-sensitive detector behind the filter records the scattered radiation. An object image is constructed based on the small-angle scattering information and the compositions of regions of the object are determined from scattering curves for the regions. One embodiment of the invention includes a source of penetrating radiation, a detector system for radiation transmitted through an analyzed object, a detector system for radiation the object scatters at small angles, and a unit for moving the object during scanning. A three-dimensional absorption factor distribution is determined for the object by X-raying the object at different angles. Small-angle scattering curves are obtained for separate volume elements of the object. The scattering curve for a volume element is compared to a data base of scattering curves for known substances to identify the composition of the element. A three-dimensional image of the object's internal structure has the substances composing the object identified. A unit shaping the radiation flux to the object can be two separate sets of collimators. One set forms fan beams for scanning the object and forming an image based on radiation absorption. The other set of collimators forms beams for imaging based on small-angle scattering and includes a series of multislit collimators. The collimators' axes are at different angles with the object motion direction. Each multislit collimator forms flat weakly diverging fan-shaped beams. Two-dimensional coordinate-sensitive detectors with a spatial filter positioned before each of the detectors record the scattered radiation.

31 Claims, 12 Drawing Sheets

INSPECTION EQUIPMENT USING SMALL-ANGLE TOPOGRAPHY IN DETERMINING AN OBJECT'S INTERNAL STRUCTURE AND COMPOSITION

BACKGROUND

1. Field of the Invention

This invention relates to methods and devices for determining the internal structure and composition of objects using small angle deflection of penetrating radiation.

2. Description of Related Art

Known absorption radiography devices determine the internal structure of an object by recording the intensity distribution of radiation transmitted through the object. Variations in the intensity distribution result from differences in radiation absorption in different paths through the object. For such devices, scattering of radiation in the object creates background noise and reduces image contrast. To offset the effect of scattered radiation, U.S. Pat. No. 4,651,002 proposed recording the scattered radiation separately using a collimator and filter, and subsequently subtracting the recorded scattered radiation intensity from the overall intensity distribution obtained when the object is X-rayed. U.S. Pat. No. 4,651,002 measures an integral of scattered intensity which does not require a fine adjustment of the relative positions of collimation and filter lattices. Accordingly, the filter is implemented as a mobile element, and the scattering is measured for large angles.

To account for background scattered radiation, U.S. Pat. No. 4,549,307 proposed special lids that block incident radiation and form spots on an object being inspected. In the spots, only the background i.e., only the scattered radiation is recorded. The background level over the entire image is approximated from measurements in the spots and is subsequently subtracted from the overall absorption signal to obtain a higher-contrast image.

As mentioned, the above-described devices identify or determine the internal structure of an object from the intensity distribution of the radiation transmitted without deflection through the object. If the object contains substances only weakly differing in absorbing properties, an image obtained using these devices may lack the contrast required to distinguish the parts of the object containing such substances, and imaging the object's internal structure may require an approach other than absorption radiography.

British patent No. 2,299,251 (1996) proposed a device using Bragg reflection from the crystal structures to identify crystalline and poly-crystalline substances. A collimator of the device allows recording of the energy spectrum for each separate region of an object through which the radiation passes. The energy spectrum distribution of the polychromatic radiation reflected at a selected angle is characteristic of the crystal structure of the substance reflecting the radiation and hence allows identification of the substance using a database of energy spectrum distributions. This method was proposed for identifying explosives in luggage. However, the method is limited to detecting substance with a crystalline or polycrystalline structure.

U.S.S.R. patent document SU 1402871 (1987) and Russian patent document RU 2012872 (1994) describe devices for imaging an object's internal structure using the effects of X-ray refraction at boundaries between parts of the object with different electronic densities. Refraction deflects X-rays by up to three seconds. These devices use single crystals to collimate the incident radiation and filter the refracted radiation. A drawback of these devices is their dependence on single crystal reflection according to the Bragg law which causes small aperture ratios. For every wavelength, the radiation is reflected at a certain angle within a deflection interval equal to the angular interval of the Bragg reflection, about ten angular seconds. This means that only a fraction (about $10^{-5}$) of the source radiation energy is used for imaging the object.

Published PCT patent application No. WO96/17240 (1996) describes devices that achieve larger aperture ratios using aperture lattices instead of single crystals. In such devices, a collimation lattice before the object forms an incident flux as a series of narrow, weakly diverging beams. A filter lattice between the object and a detector acts as a scattering radiation filter. The two lattices are positioned with respect to each other so that the penetrating radiation flux in the absence of an analyzed object would not reach the detector. During imaging, the object is immobile with respect to the detector, and the spatial frequency and positions of the detecting rays determine the positions and sizes of the X-rayed parts of the object. The collimation lattice is preferably large enough to encompass the entire object and should have the opaque regions no more than 0.05–0.1 mm wide to ensure a suitable resolution for detecting inhomogeneities in the analyzed object. These two requirements of the collimation lattice increase the device cost and complicate adjustments of the device.

U.S. Pat. Nos. 4,751,772, 4,754,469, 4,956,856, 5,008,911, and 5,265,144 describe methods and devices for examining biological tissues and identifying explosives in luggage by recording the spectra of coherent radiation scattered at angles within 1° to 12° of an incident beam direction. A large part of the elastically scattered radiation is within those angles if the X-ray energy is small enough. As specified in those patents, analysis of the object uses a narrow collimated beam of monochromatic or polychromatic radiation. The intensity of the coherently scattered radiation is measured using a detecting system resolving both the energy and the scattering angle of the radiation. Several principles underlie these devices, one of which is that the energy spectra of elastically scattered radiation (unlike inelastically scattered Compton radiation) are identical to the spectrum of the primary beam. The intensity of the elastically scattered radiation has a characteristic angular variation with a pronounced maximum in the angular interval from 1° to 19°. The maximum defection angle depends on the X-rayed substance and the energy of the incident radiation. Since the intensity distribution of the coherently scattered radiation for small scattering angles depends on the molecular structure of the object substance, substances with the same absorbance (which conventional absorbance X-ray analysis cannot distinguish) can often be discriminated by the intensity distribution of the angular scattering of coherent radiation.

U.S. Pat. Nos. 4,751,722 and 4,754,469 describe devices using small-angle coherent scattering and computer tomography to form an image. The described devices have relatively low sensitivities since the coherent scattering cross-section is small in the specified angular range, therefore high radiation doses are required to X-ray an object. U.S. Pat. No. 5,265,144 describes a device using concentric detecting rings for recording the radiation scattered at particular angles. That device X-rays an object using a narrow beam with a small divergence, which is required for successful recording of the small-angle scattering, and has the problem of the small aperture ratio and, consequently, low sensitivity. The radiation flux in the described devices scatters off of different materials encountered during passage through the object, so that intensity distributions are superpositions of several curves resulting from different materials contained in the object. This complicates the substance identification from scattering curves. U.S. Pat. No. 4,752,722 proposes solving this problem using small-angle computer tomography. However, forming a tomographic image requires X-raying an object from a large number of different angles (0 to 360 degrees) which is expensive and not always feasible.

This invention aims to obtain information on substance distribution over the volume of an analyzed object using a relatively inexpensive device having a high aperture ratio. Further, the invention aims to create a device that is easier to produce and operate while having enhanced image quality when imaging or forming a projection of an object's internal structure.

SUMMARY

One embodiment of the invention forms a small-angle topogram which is essentially a picture or projection of an objected formed using radiation coherently scattered at small angles in the object. Additionally, scattering curves are determined for multiple beams traversing the object at different angles. The scattering curves relate each image point to the diffraction properties of a part of an object through which an associated radiation beam passed. The scattering curves and the topogram indicate small-angle scattering intensity and thus carry information about the molecular composition of the object. In the measurements, each scattering intensity is a superposition of several scattering curves from different object areas through which the radiation beam passes. This hampers analysis of the object. However, using scattering curves detected for beams traversing the object along different directions, tomographic techniques can determine approximate scattering curves $I(\theta)$ for specific points or regions of the object. The more the detectors, i.e., the larger the number of angles at which the scattered radiation intensities are measured, the more exact is the scattering curve approximation. Each substance has a unique scattering curve, and scattering curves of substances of interest can be entered into a database. By comparing an obtained approximate scattering curve with scattering curves in the database, the substance contained in a specific region of an object can be identified The principles of the invention can be implemented variety of devices. One such device is a small-angle topography device that includes: a source of penetrating radiation; a collimator forming the incident radiation flux as a series of narrow, weakly-diverging beams incident on an object; a spatial filter behind the object; and a coordinate-sensitive detector behind the filter. The collimator has areas transparent to the radiation, e.g., slits or channels, alternating with areas opaque to the radiation. The spatial filter is a regular periodic structure similar to the collimator but has the areas of opaque material corresponding to the transparent areas of the collimator so that the opaque areas of the filter block radiation on direct paths from the transparent areas of the collimator. Each beam from the collimator covers a separate area in an object projection. The device further includes a facility for moving the object relative to the penetrating radiation beam, to scan the object and obtain the complete projection of the object on the detector.

In one embodiment, the collimator includes a regular periodic structure consisting of areas opaque to the radiation and the transparent channels. The shapes and positions of the channels can differ but can be, for example, slits or circular orifices positioned in a hexagonal pattern. A slit collimator can include alternating plates opaque to the radiation with gaps between the plates or alternatively two diaphragms where an input diaphragm has one or several slits and an output diaphragm has multiple slits. Alternatively, a collimator having transparent channels with circular apertures can be implemented either as a capillary twist, or as two diaphragms, an input diaphragm with one or several orifices and an output diaphragm with many orifices. To form beams with micron or submicron thicknesses and divergences of a few angular minutes, a slitless collimator uses the X-ray transmission effect at the border of two flat polished plates, with repeated complete internal reflection (CIR). A slitless collimator is implemented as a set of metal or glass plates with polished surfaces stacked on top of each other without gaps, and pressed together under high pressure. To obtain extremely narrow (with divergences less than ten angular seconds) high-intensity X-ray beams, a modified collimator includes a stack of the polished-surfaced plates having unpolished bands on the reflecting surfaces perpendicular to the X-ray path.

The spatial filter is a regular periodic structure complementary to the collimator, i.e., the spatial filter is arranged to screen the direct radiation from the collimator, and transmits the radiation that the object scatters at angles in a desired range. The spatial filter should be implemented as a linear raster for a slit collimator, and as a raster with round opaque regions for a collimator with cylindrical channels.

The collimator directs separate beams of penetrating radiation to separate areas of the analyzed object, so that relative motion of the object across the beams is needed to obtain the complete picture of the object's internal structure. The facility for moving the object should therefore be a device ensuring uniform motion of the object across the scanning rays with a velocity sufficient to obtain the necessary exposure on the detecting device. The detecting device is a coordinate-sensitive X-ray radiation sensor that simultaneously registers information from all beams. An information processing system receives collects information from the detector and creates an object image with contrast indicating differences in the small-angle scattering. That image can be compared to an image obtained in the absorption contrast. For separate elements in the object, the processing system determines small-angle scattering curves and compares the determined curves to an available book or database of scattering curves of known substances. The processing system identifies the substance of an element when a matching scattering curve is found in the data base.

Another embodiment of a device for small-angle topography includes a radiation source, a slit collimator forming the incident flux as a number of small, weakly diverging beams incident on an object, and a spatial filter positioned behind the object where detector elements are disposed in the spatial filter. The spatial filter can be a slit raster made of opaque plates with the registering elements placed in the slits. The widths of the plates are selected to ensure the scattered radiation from one beam does not affect the registering elements for a neighboring beam. The depths and widths of the gaps between the plates are such that each individual detector registers radiation falling on a definite angular ranges. One embodiment includes three gaps and three detector elements per incident beam. A central detector element for a beam measures the intensity of the radiation transmitted directly through the object. The other two detector elements for the beam measure the intensity of radiation deflected into the desired angular range to either side of the central element. Each of the detector elements is connected to a processing system that separates intensity information associated with the radiation scattered by the object from intensity information associated with undeflected radiation. Two images can be formed on a monitor, one image corresponding to the small-angle contrast of the object, the other corresponding to the absorption contrast.

A method for examining an object, X-rays the object at different angles and determines a three dimensional distribution of the absorption factors of the object Additionally, a small-angle scattering curve is obtained for each object element. To determine the absorption factors, the object (which for example, can be luggage that is being checked for explosives) is scanned by flat fan-shaped beams of penetrating radiation from a single source directed at various angles that are as different as possible from each other. The scanning can be performed by moving the optical elements of the device (e.g., the collimator, spatial filter, and detector), or by moving the object. Moving the object is typically more practical in luggage control devices. The thickness of each beam is selected according to the required resolution of the device i.e., according to the size of an area that the substance to be identified occupies in the object. The width of each of the flat beam in the direction perpendicular to the scanning direction encompasses the entire analyzed object.

For each beam, a coordinate-sensitive detector records the intensity of the radiation transmitted through the object. The detector can be a system of linear detecting elements oriented parallel to the plane of the incident beam. With that orientation, the spatial resolution of the coordinate-sensitive detectors determine the minimum size of revealed inhomogeneties. As the object moves, each beam successively scans the entire object. The intensity of the radiation transmitted through the object depends on absorption factors of the substances the beam crosses. From the measured transmittance of beams crossing the same object cell at different angles, an average absorption factor can be determined for the substances filling that cell. The values of the measured intensities of the radiation transmitted through the object is transferred into the processing system that calculates the distribution of the absorption factors over the entire object volume. The object is then represented as a three-dimensional matrix of elementary cells, each having a constant absorption factor.

Each of the cells is considered to be filled with one substance only. From the obtained absorption factor distribution, average atomic numbers can be determined for the substances in the cells. Since different substances may have similar absorption factors, the object image obtained in this mode of X-raying may be unable to discriminate between the substances with similar absorption factors.

To discriminate between substances having similar absorption factors, coherent small-angle scattering (SAS) is used. The small-angle scattering curves appearing for individual beam when a complex object is X-rayed are superpositions of scattering curves of all the substances crossed as a beam passes through the object. To isolate the scattering curve of a single object cell from the superposition, small-angle intensity distributions are obtained for several angles of incidence of the beams onto the object, with those angles differing as much as possible from each other. A separate SAS system can be used for each beam. Each SAS system includes a collimator, a spatial filter, and a coordinate-sensitive detector to measure small-angle scattering curves for the beams formed by the collimator. Each collimator forms a series of narrow, weakly diverging beams from the single source. The object successively passes through the SAS systems so that each of the systems scans the object.

Processing the small-angle scattering curves measured for beams at different scanning angles yields a distribution of scattering curves characterizing the structure and composition of the object.

Measuring the small-angle scattering intensity at several different angles and then constructing the corresponding approximate scattering curves for each cell (or volume element) in the object allows identification of the substance in the cell. The accuracy of the approximation of a cell's scattering curve is higher for larger numbers of angles for which the coherent scattering intensities are measured. The range of the measured small-angle scattering can be limited to the angular region in which the major part of the coherently scattered radiation is located, namely, the so-called central diffraction peak region. This region may be from 5 angular seconds to 1 degree depending on the wavelength used and the structural properties of the material. Recording small-angle scattering in the central peak region provides greater intensity for the recorded radiation. When calculating the scattering curves for each cell, allowance can be made for differences in measurement conditions such as differences in absorption before a primary beam reaches the cell, and attenuation of the deflected beam on the way from the cell to the detector. The allowance are made using the determined absorption factors. The scattering curves obtained for each cell are averages for different beams. Substances are identified for each cell, first, by absorption factor and the small angle scattering curve. Cells having absorption factors that do not correspond to a sought substance can be excluded from consideration analysis of SAS measurements. For instance, when searching luggage, regions that absorption factors indicate are metals or ceramics may be excluded from SAS analysis searching for explosives or drugs. This simplifies and accelerates the procedure by limiting analysis of SAS data to cells of interest as identified from absorption data. The processing system can create object images from two types of information, absorption factors and small-angle scattering curves. By combining the two types of images, the data processing system can determine the three-dimensional internal structure image of the object, with identification of the substances composing the object and graphically display the internal structure and composition on a display screen.

The total number of different SAS systems used in the device is selected according to the complexity of the analyzed object. For example, in luggage control, the overall number of substances present in each analyzed object, typically does not exceed thirty. Four analyzing beams 40° apart from each other are sufficient to determine absorption factors of the substances, and the SAS systems can be positioned in spaces between the individual beams for absorption measurement. The overall spread of the system is about 120°.

One embodiment of the invention contains a source of penetrating radiation, a system measuring radiation absorption in the analyzed object, a system measuring radiation scattered at small angles, and a device for moving the object for scanning. The system for measuring absorption in the analyzed object consists of a slit collimator forming fan-shaped beams, a filter positioned behind the object to eliminate background radiation to improve the image contrast, and a number of coordinate-sensitive detectors. Each detector records the intensity of the transmitted radiation for a separate beam and has spatial resolution along a direction parallel to the plane of the incident beam. The dimensions of each collimator slit determines the width and angular divergence of the beam and should be such that the size of the incident beam on the object in the scanning direction is less than the minimal size of a inhomogeneity to be detected. Otherwise, a substance may not be discriminated from background of a surrounding medium. The size of the beam projection in the direction perpendicular to the scanning direction should be no less than the object dimensions. For each beam, a coordinate-sensitive detector records the radiation transmitted through the object during the whole period of object scanning. The measured intensities of the transmitted radiation for different angles of beam incidence onto the object are transferred into the data procession system where the object image is constructed from intensity values of the transmitted radiation in the form of an absorption factor distribution over three-dimensional matrix elementary cells.

The measuring system for the small-angle scattering from the object uses penetrating radiation from the same source and identical blocks positioned at different angles to the direction of the scanning motion. Every such block contains a collimator, a spatial filter, and a two-coordinate coordinate-sensitive detector. Each collimator is between the source and the object and shapes the radiation flux into one or several narrow weakly diverging beams falling on the object. A multislit collimator is a regular periodic structure consisting of regions transparent to the radiation alternating with opaque regions. The lines of the surfaces forming the opaque regions should converge at the focal spot of the source for every collimator to increase the energy efficiency of the device. Accordingly, the radiation reaching different slits of the collimator may be emitted by different parts of the source focal spot. To isolate the radiation that the analyzed object scatters at small angles, a spatial filter, which is positioned before the coordinate-sensitive detector, matches the collimator and blocks direct radiation as described above.

The collimator forms beams penetrating particular parts of the object, so it is necessary to move across the detecting beams to obtain the whole image of the object's internal structure in the beams scattered by small angles. A conveyor, for example, moves the object through the systems for measuring the absorption and small angle scattering, with a speed slow enough to provide the necessary exposure times for the detectors in both systems. The detecting device for recording the small-angle scattering is a two-dimensional coordinate-sensitive X-ray element that can be a charge-coupled device, photodiode matrix, a luminescent screen, or X-ray film. The detector sensitivity determines the required power of the radiation source and the speed of scanning the object. The data processing system receives a data signal from the coordinate-sensitive detector and forms the object's image according to the intensity of small-angle scattering which can be compared to the image obtained from absorption. Small-angle scattering curves obtained for individual cells in the object are compared with the available data base of small-angle scattering curves to identify the substances in the cells.

In another embodiment of the invention, for every fan-shaped beam directed to the object at a definite angle, both the radiation transmitted without absorption and the intensity distribution of small-angle scattering are recorded simultaneously. As in the above-described embodiment, a series of narrow weakly diverging beams is formed from a single source of penetrating radiation using a collimator. Radiation is recorded using detecting elements (e.g., a bar of charge-coupled elements or X-ray range photodiodes) positioned deep inside a raster of slits made of plates opaque to the radiation. The plate thicknesses are selected to eliminate the influence of the radiation scattered from one beam to a recording element for the neighboring beams. The depths and widths of gaps between the plates is determined by the requirement for the individual detector to register radiation falling onto it at a specific angle.

BRIEF DESCRIPTION OF THE DRAWINGS

Use of the same reference symbols in different figures indicates similar or identical items.

DETAILED DESCRIPTION OF THE PREFERRED EMBODIMENTS

Figure 1:
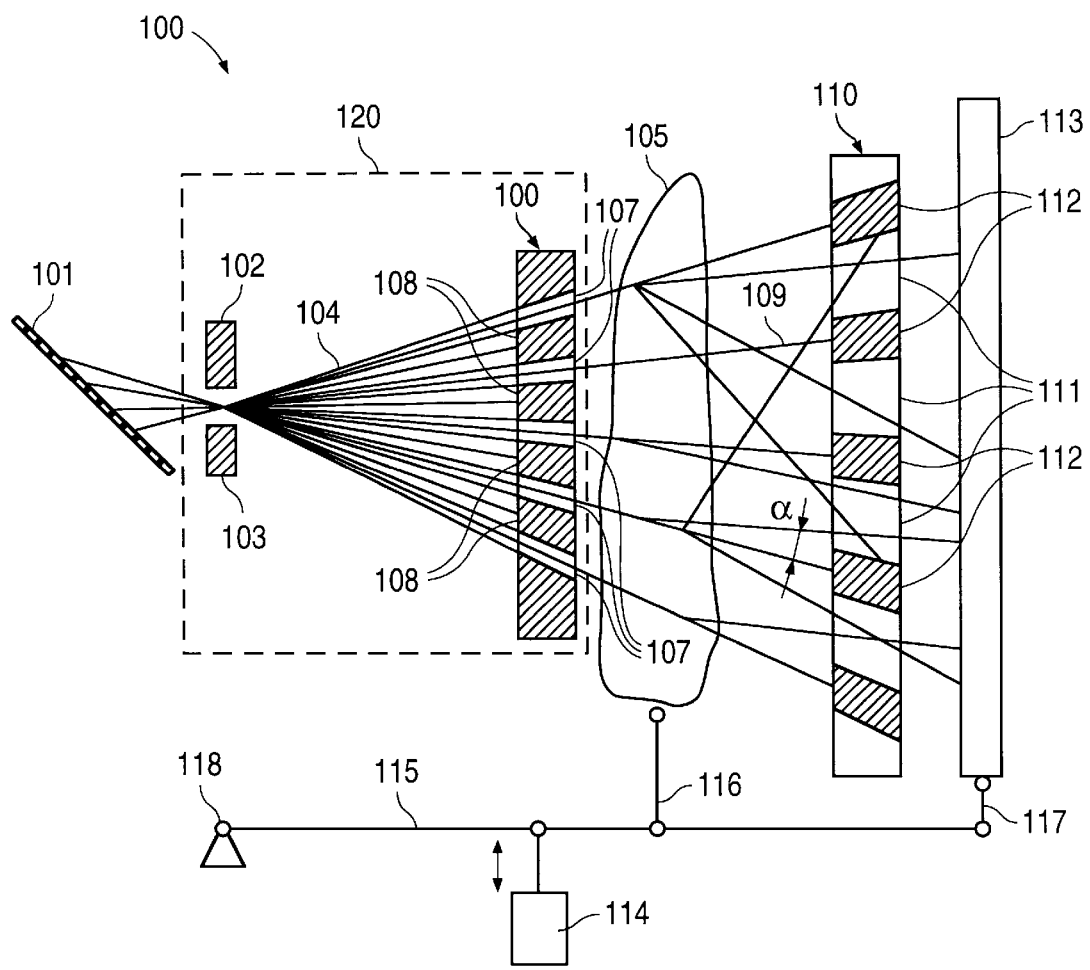
FIG. 1 shows a small angle topography device in accordance with an embodiment of the invention.

FIG. 1 shows a small-angle topography device 100 that includes a source 101 of penetrating radiation, a collimator 120 including diaphragms 102 and 106 that shape radiation incident on an analyzed object 105, and a spatial filter 110 between object 105 and a coordinate sensitive detector 113. Source 101 in an exemplary embodiment of the invention is an X-ray tube that directs X-rays at diaphragm 102. Alternatively, source 101 can be any type of X-ray radiation source, provided radiation 104 has the hardness and the intensity necessary to X-ray object 105. For collimation, diaphragm 102 is a sheet of a material such as tungsten or lead that is opaque to the penetrating radiation. In diaphragm 102, an orifice 103, which may be a slit, circular, or any desired shape, limits the divergence of radiation 104 that passes to diaphragm 106. Diaphragm 106 has alternating regions 107 and 108 that are respectively transparent and opaque to the penetrating radiation. Transparent regions 107 may be empty openings in diaphragm 106 or filled with a transparent material such as a polymer. Radiation passing through transparent regions 107 is incident on object 105. Collimator 120 and spatial filter 110 are interrelated and determine many of the device's operation parameters. For example, the focal spot of source 101 has dimensions that depend on the configuration of collimator 120 and spatial filter 110.

Spatial filter 110 has transparent regions 111 and opaque regions 112 in the path of radiation 109 that passes through object 105. Transparent regions 111 of spatial filter 110 transmit the coherent radiation scattered at small angles. Opaque regions 112 absorb the direct radiation from associated transparent regions 107 of collimator 120 (i.e., the radiation that passes through object 105 without being deflected) and radiation scattered at large angles. Accordingly, in the absence of object 105, detector 113 registers only a background intensity signal. When object 105 is in the region between collimator 120 and filter 110, object 105 scatters radiation and creates an image signal on detector 113. The intensity distribution of small-angle scattered radiation obtained on coordinate-sensitive detector 113 carries information about the structure of object 105 and indicates the scattering ability of substances contained in object 105. (As used herein, the term "coordinate-sensitive detector" indicates a detector that records separate intensities or measurements at different coordinates on the detector.) For identification of substances present in object 105, measured small-angle scattering curves can be compared to a data base of scattering curves for selected known substances. The data base may contain for example, a set of scattering curves where each curve is represented by a table of intensities indexed by angel and corresponds to a substance to be detected such as an explosive material or controlled substance.

Collimator 120 forms narrow, weakly diverging beams and includes a regular periodic structure consisting of areas 108 opaque to the radiation and transparent channels through areas 107. The shapes and positions of the channels can differ but can be, for example, slits or circular orifices positioned in a hexagonal pattern. The suitable spacing and shapes for the channels in the collimator depend on nature of object 105. General requirements for collimators 120 are as follows. First, lines of the surfaces forming the transparent channels should converge at the focal spot of source 101 to enhance the energy efficiency of device 100. The radiation reaching different collimator channels may result from different parts of the focal spot thus permitting use of powerful wide-focus sources. Second, collimator 120 should form beams with a divergence γ small enough to permit detection of radiation scattered in a desired small-angle range, in particular, to ensure that every beam that object 105 scatters by more than a minimum angle α is outside the primary flux. Third, the structure of collimator 120 should be such that scattering within the desired range of angles from neighboring beams do not overlap each other at detector 113. This ensures clear detection at small angles up to an angle β. (Angles α and β determine the desired small-angle range, with angle α typically of 5 angular seconds of more and angle β being up to 1° or more.) To satisfy these requirements, collimator 120 and spatial filter 110 should be separated by a distance larger than the cross dimensions of collimator 120.

Figure 2:
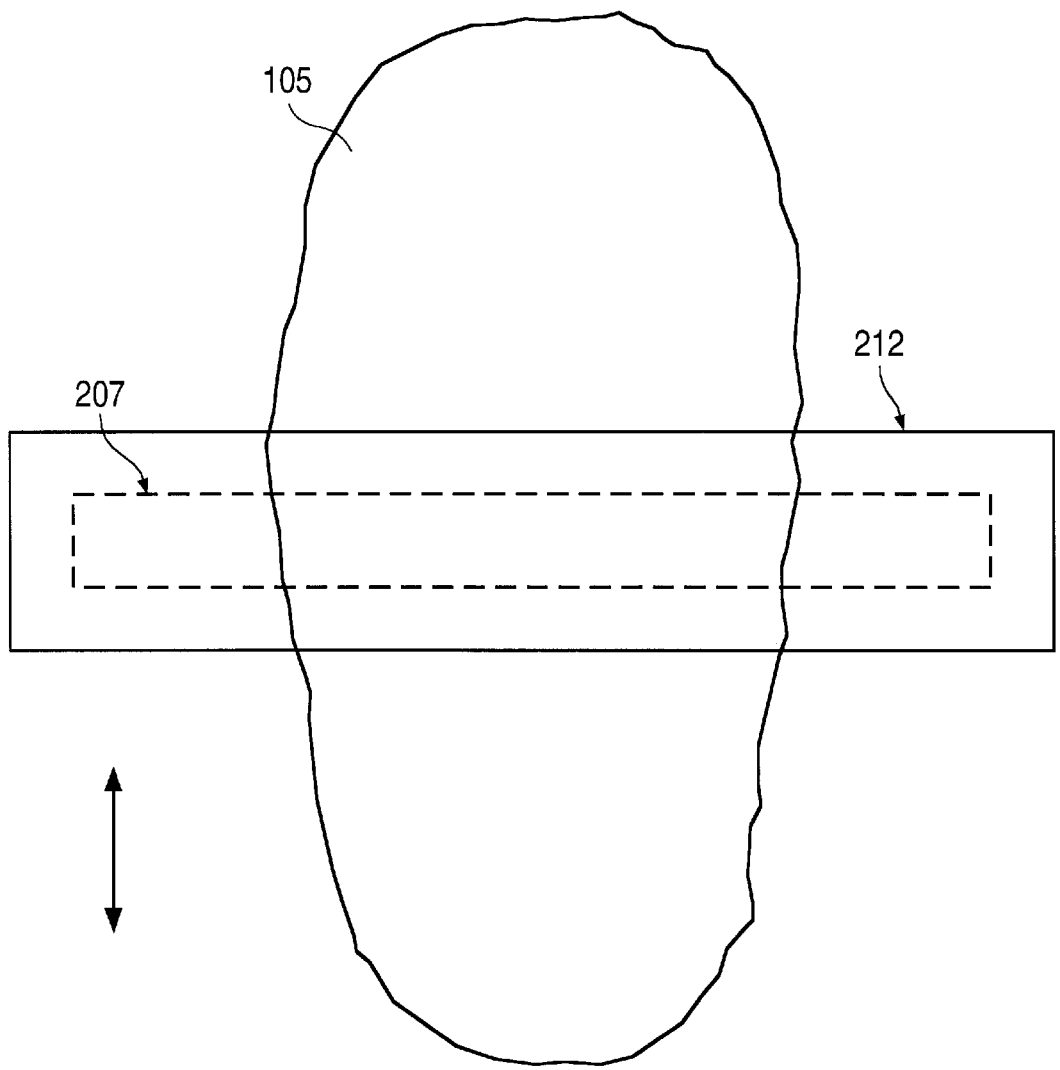
FIG. 2 shows cross sections of a fan beam from a collimator that is opaque except for one or more slit-shaped transparent regions.

A slit collimator (i.e., a collimator having transmission channels in the shape of slits) can include plates opaque to the radiation and gaps between the plates, or two diaphragms including an input diaphragm having one or several slits and an output diaphragm having multiple. FIG. 2 illustrates the relation of a cross-section 207 of radiation at a slit in a collimator to a cross-section 212 of the primary radiation at a spatial filter behind object 105. In regard to FIG. 1, a transparent region 107 of output diaphragm 106 controls the size of cross-section 207, and spatial filter 110 has an opaque region 112 matching the size and position of cross-section 212.

A slit in a collimator illuminates only a band of object 105 at a time, but scanning the band of radiation across object 105 provides data on the structure of the entire object. Two ways to scan object 105 are moving the optical elements of the device relative to object 105 and moving the object 105. Moving object 105 is preferred because moving the optical elements (collimator 120 and filter 110) may cause vibrations that shift the relative position of opaque region 112 and matching transparent region 107. In FIG. 1, a drive 114 rocks a lever 115 that is hinged at one end 118 and connected to object 105 and detector 113 by hinged traction bars 116 and 117, respectively. To preserve the scale and relative position of the image of the internal structure of object 105 formed on detector 113, displacements of object 105 and detector 113 are synchronous and proportional to the distance from the divergence point of source 101 to object 105 and to detector 110 respectively.

Figure 3:
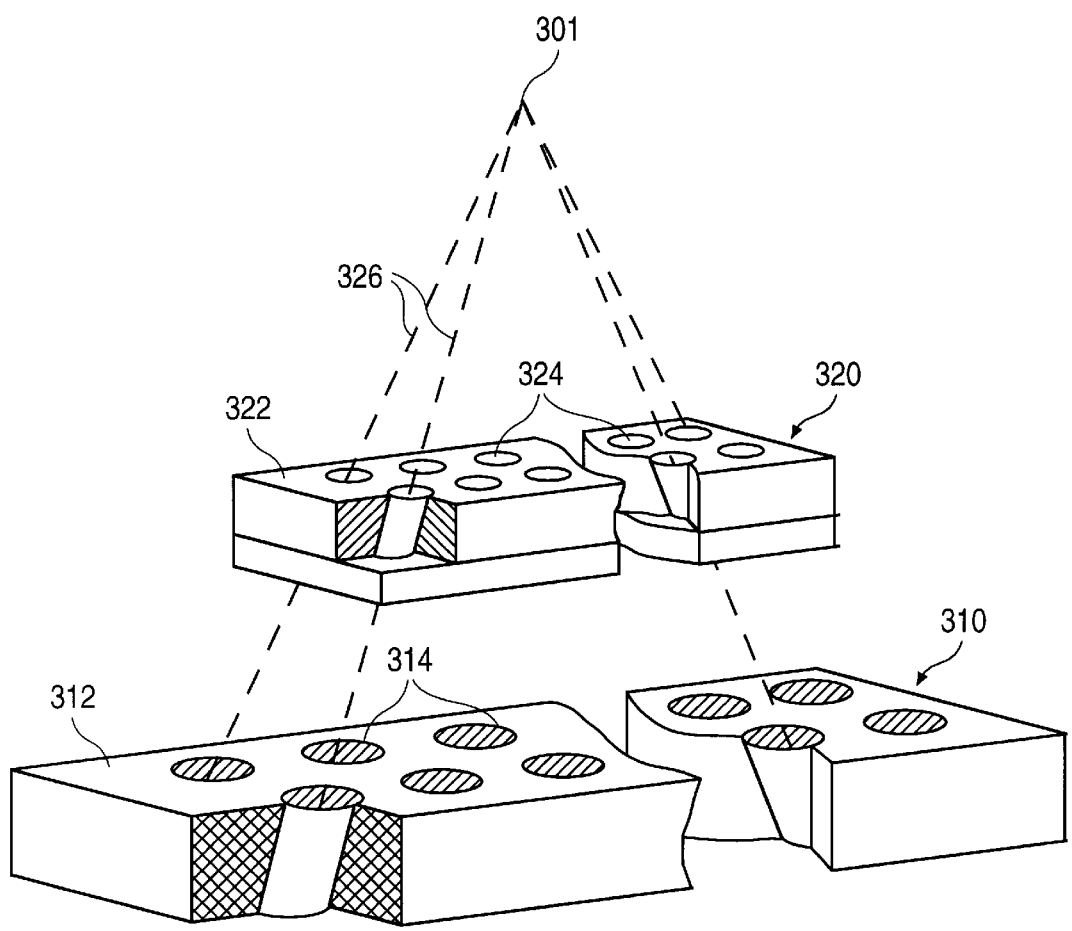
FIG. 3 shows a collimator which in accordance with an embodiment of the invention is formed from a block of opaque material with transparent channels or aperture.

An alternative collimator configuration has radiation-transparent channels with circular apertures. Such collimators can be implemented either as a capillary twist, such as available from X-ray Optics, Inc. of Albany, N.Y. or as two diaphragms, an input diaphragm with one or many orifices and an output diaphragm with many orifices. FIG. 3 shows a collimator 320 and a spatial filter 310 for beams with circular profiles. In FIG. 3, collimator 320 is a block 322 of material opaque to the radiation with transparent channels 324. Axes of channels 324 are along lines 326 converging at a point 301 that coincides with the source focus of the radiation source. Spatial filter 310 matches collimator 320 and is a block 312 of material transparent to the radiation having regions 314 in block 312 filled with a material opaque to the radiation such as tin, tungsten, titanium, or lead. Axes of regions 314 are also along lines 326 converging at point 301.

Blocks 322 and 312 can be manufactured using photolithography and etching. To manufacture block 320, projections in (or surrounding) the regions of channels 324 are made in a plate of a polymer transparent to penetrating radiation. The projections can be inclined to the surface of the plate at angles originating from a source focus. The plate is then etched to remove unexposed portions (or exposed portions depending on the material in the plate) of the plate. The removed portions are then filled with a material opaque to the penetrating radiation, e.g., tungsten powder. Similarly, to manufacture block 312, inclined openings in regions 314 are made through a plate made of a polymer transparent for the penetrating radiation, and the openings are filled with a material opaque to the penetrating radiation. The dimensions of the channels (in this case, their depths and diameters), the collimator structure period (the distance between the collimator channels), and dimensions of the opaque regions of block 312 are selected so that only the radiation corresponding to small-angle scattering in the analyzed object reaches the coordinate-sensitive detector.

A slitless collimator forms beams with thicknesses of a micron or less and divergences of a few angular minutes. A slitless collimator, which uses the X-ray transmission effect caused by complete internal reflection (CIR) at the border of two flat polished plates, can be implemented as a set of metal or glass plates with polished surfaces stacked on top of each other without gaps and pressed together under high pressure.

Slitless collimators have high aperture ratios and allow beams 1 to 2 µm wide. The lengths of the plates in the direction of X-rays propagation allow complete absorption of the part of the beam not passing along the boundary between the plates (the working plane). For perfectly flat and smooth plates, the effective width of a channel along which the X-rays propagate in a slitless collimator, is determined by the penetration depth of the radiation into the medium during CIR, which is from tens to hundreds of angstroms. Practically, this value depends on the polishing quality and flatness of the plates, and conditions of their pressing. The divergence 2γ of the beam passed through a slitless collimator is equal to the input aperture angle of the collimator but cannot exceed the twice the CIR critical angle, 2θ. The input aperture angle is determined as $$2\delta = f/D$$

where f is the focus size of the X-ray tube along the direction perpendicular to the collimator working plane; D is the distance from the tube focus to the collimator input.

A modified slitless collimator provides extremely narrow (with divergences less than ten angular seconds) high-intensity X-ray beams. This collimator also consists of a stack of the polished-surfaced plates pressed together, but unpolished bands are made on the reflecting surfaces perpendicular to the X-ray path, and located at such distances from the device input and output as to be able to completely absorb the beams. After the beams pass through the input boundary of the polished surfaces according to CIR, the beams proceeding at larger angles fall onto the unpolished regions of the surfaces which absorb the radiation. However, the beams proceeding at smaller angles reach the collimating device output because they do not fall on the unpolished surfaces.

The small-angle scattering spatial filter is a regular periodic structure complementary to the collimator i.e., the spatial filter is arranged to screen the direct rays formed by the collimator, and transmits the radiation scattered in the object at angles in the range from α to β. The spatial filter matches the collimator. For a slit collimator or slitless collimator, the spatial filter should be implemented as a linear raster while for the tightly packed cylindrical channels as a raster with round apertures.

Figure 4:
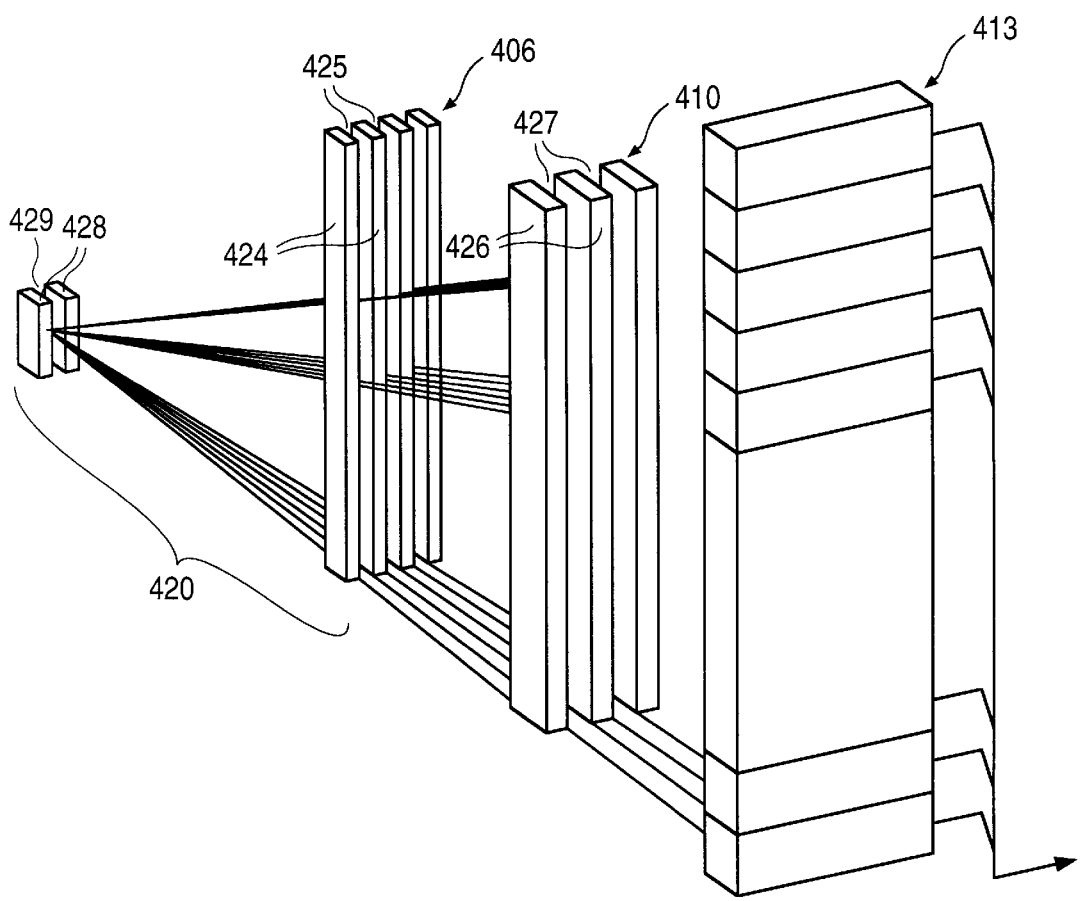
FIG. 4 illustrates relative positions of a collimator, a spatial filter, and a coordinate sensitive detector in an analyzer using fan beams in accordance with the invention.

FIG. 4 shows another embodiment of a collimator 420 and a spatial filter 410. In this embodiment, collimator 420 includes a set of plates 424 of a material opaque to the radiation positioned adjacent to each other with gaps 425 between plates 424. The thickness of plates 424 along the direction of the radiation depends on the absorption of the penetrating radiation by the material of the plate. Plates 24 have a length sufficient to cover the entire projection of the analyzed object. A diaphragm 428 having one or several slits 429 that are parallel to plates 424 and form the radiation flux to plates 424. Use of several slits in diaphragm 428 increases the percentage of radiation from the radiation source used for illumination of the analyzed object. Spatial filter 410 consists of a set of plates 426 made of a material opaque to the penetrating radiation. Gaps 427 between plates 426 form slits transparent to the radiation. Each of plates 426 has a thickness along the direction of radiation propagation selected according to the ability of the material to absorb the radiation, a length that covers the entire projection field of the object, and a width sufficient to block direct radiation from an associated gap 425 in collimator 420. Absorbing plates 426 collectively screen all penetrating radiation direct from gaps 425 so that a two-dimensional detector 413, which is behind spatial filter 410 measures only the intensity of scattered radiation.

Figure 5:
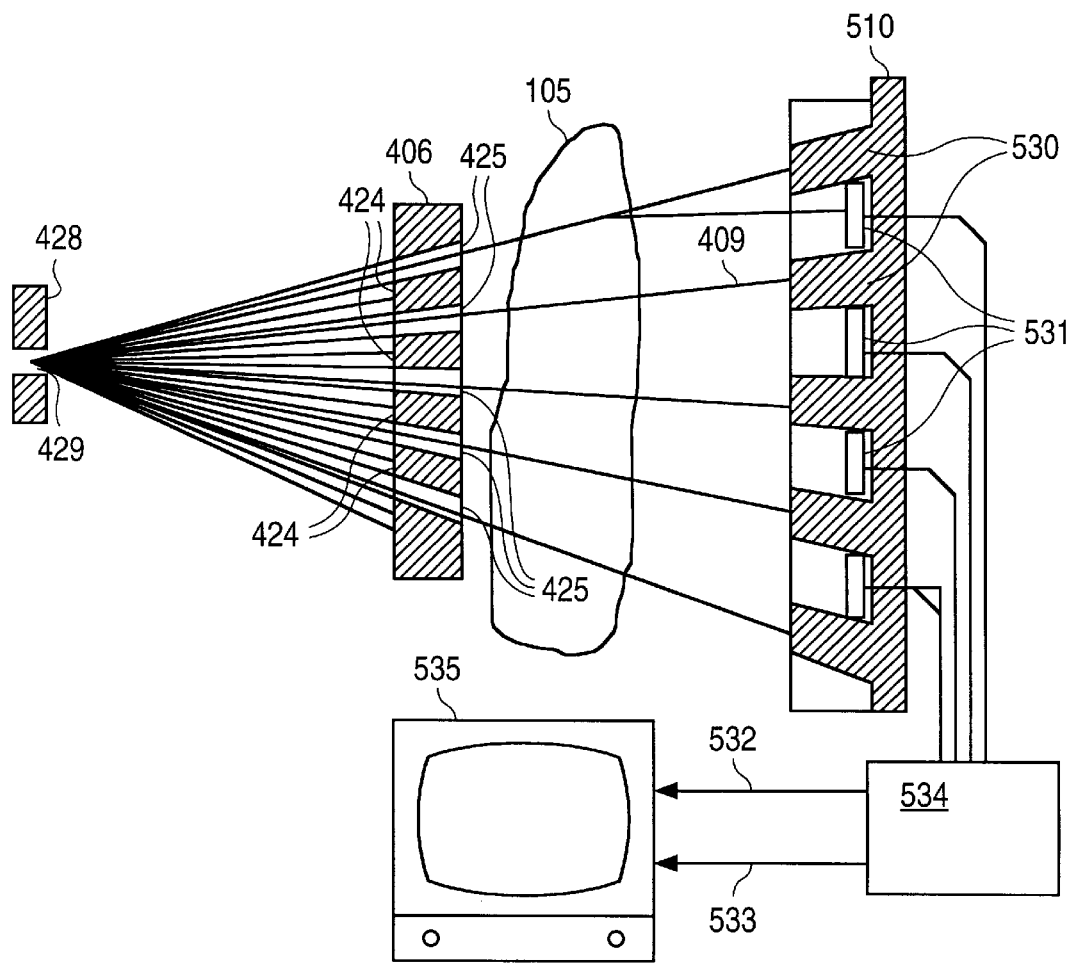
FIG. 5 shows a system having a spatial filter which in accordance with an embodiment of the invention is a set of plates with detector elements placed in slits between the plates.

FIG. 5 shows an embodiment of an imaging system where a spatial filter 510 is a set of plates 530 opaque to the penetrating radiation and gaps between plates 530 contain bars of radiation detectors 531. Each of the radiation detectors 531 corresponds to a beam from collimator 420, and plates 530 have thicknesses set to stop the radiation scattered from one beam from reaching the detector 531 corresponding to a neighboring beam. The width and length of each gap between plates 530 select a specific angular range of radiation that reaches the detector 531 in the gap. A processing system 534, which may be a general purpose computer or specialized processing equipment, records and processes measured intensities from detectors 531. Processing system 534 forms image signal 532 and 533 corresponding to radiation passed through object 105 without scattering and radiation scattered by object 105. In signal 532, the contrast results from the differences in absorption coefficients of the materials in object 105, while signal 533 indicates contrast in the intensity of small-angle scattering. In one application, the intensity in small scattering corresponds to one specific angle from each of the determined scattering curves. For example, intensity in the image could represent intensity of radiation at a specific angle that is a scattering maximum for a selected substance so that the image selectively highlights the selected substance. Alternatively, intensity at a point in the image could represent an integral of the scattering curve corresponding to the point. As yet another alternative, regions of an object identified as containing a particular substance can be assigned a false color associated with the substance. A display 535 displays the two images of the object's internal structure.

Figure 6:
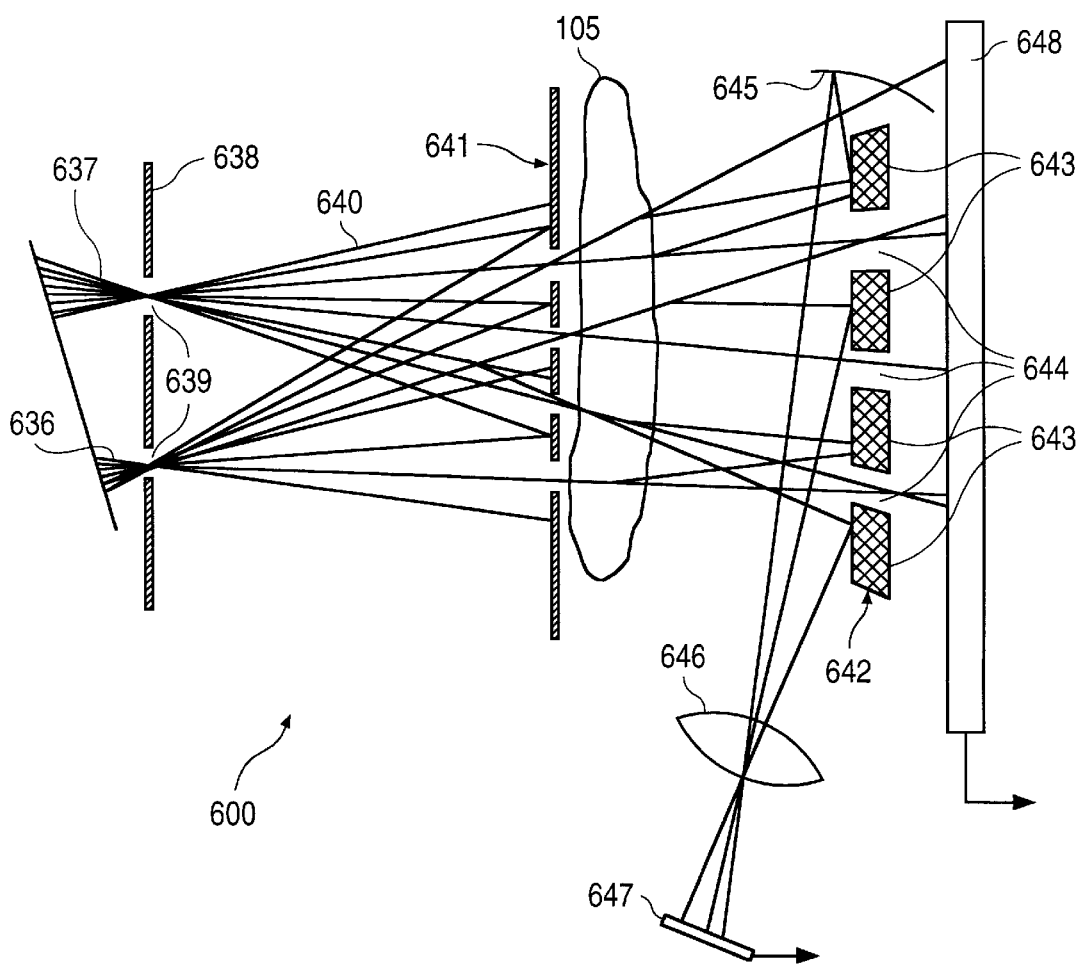
FIG. 6 shows a system in an embodiment of the invention in which penetrating radiation that passes undeflected through an object is converted into visible light.

FIG. 6 illustrates another small-angle topography device 600. Device 600 contains a source 636 of penetrating radiation and an input diaphragm 638 positioned in the path of radiation flux 637 from source 636. Input diagram 638 has several slits 639 that form a radiation flux 640 falling on object 105. An output diagram 641 between diaphragm 639 and object 105 forms many narrow weakly-diverging beams directed to analyzed object 105. Behind object 105, a spatial filter 642 includes a set of parallel plates 643 with gaps between plates 643 forming many slits 644. Plates 643 of the filter 642 are coated with a phosphor and located in the areas that diaphragm 641 shadows from penetrating radiation flux 644. The phosphor on the surface of plates 643 transforms the penetrating radiation scattered by object 105 into visible light. The light then passes through an optical system including a concave mirror 645 and a collecting lens 646 to a detector 647 which registers the intensity distribution of the radiation scattered as indicated by the distribution of visible light from plates 643. Device 600 can thus forms two images of the internal structure of the analyzed object. One image determined from the distribution of scattered radiation forms on detector 647, and another image determined from the direct radiation passing through object 105 to a detector 648 behind plates 643. This provides more complete information about the object's internal structure.

Collimators in the above described embodiments direct separate beams of penetrating radiation to separate areas of the analyzed object, and relative motion of the object across the beams is needed to obtain a complete image of the object's internal structure. The facility for moving the object should be a device ensuring uniform motion of the object across the scanning rays with a velocity sufficient to obtain the necessary exposure on a detector. The detector is a coordinate-sensitive X-ray radiation sensor that simultaneously registers information from all the beams. The detector could be, for example, a photodiode matrix, a luminescent screen, or X-ray photographic film.

Figure 7A:
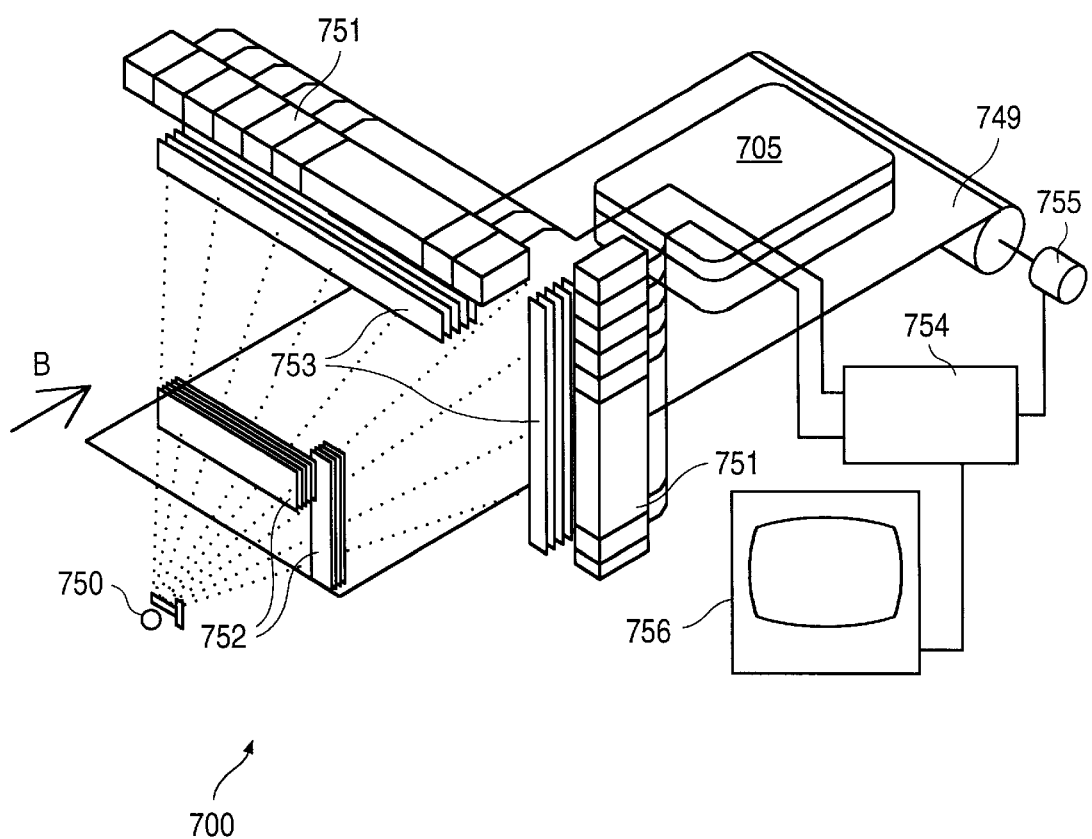
FIGS. 7A and 7B show different views of a luggage control facility in accordance with an embodiment of the invention.
Figure 7B:
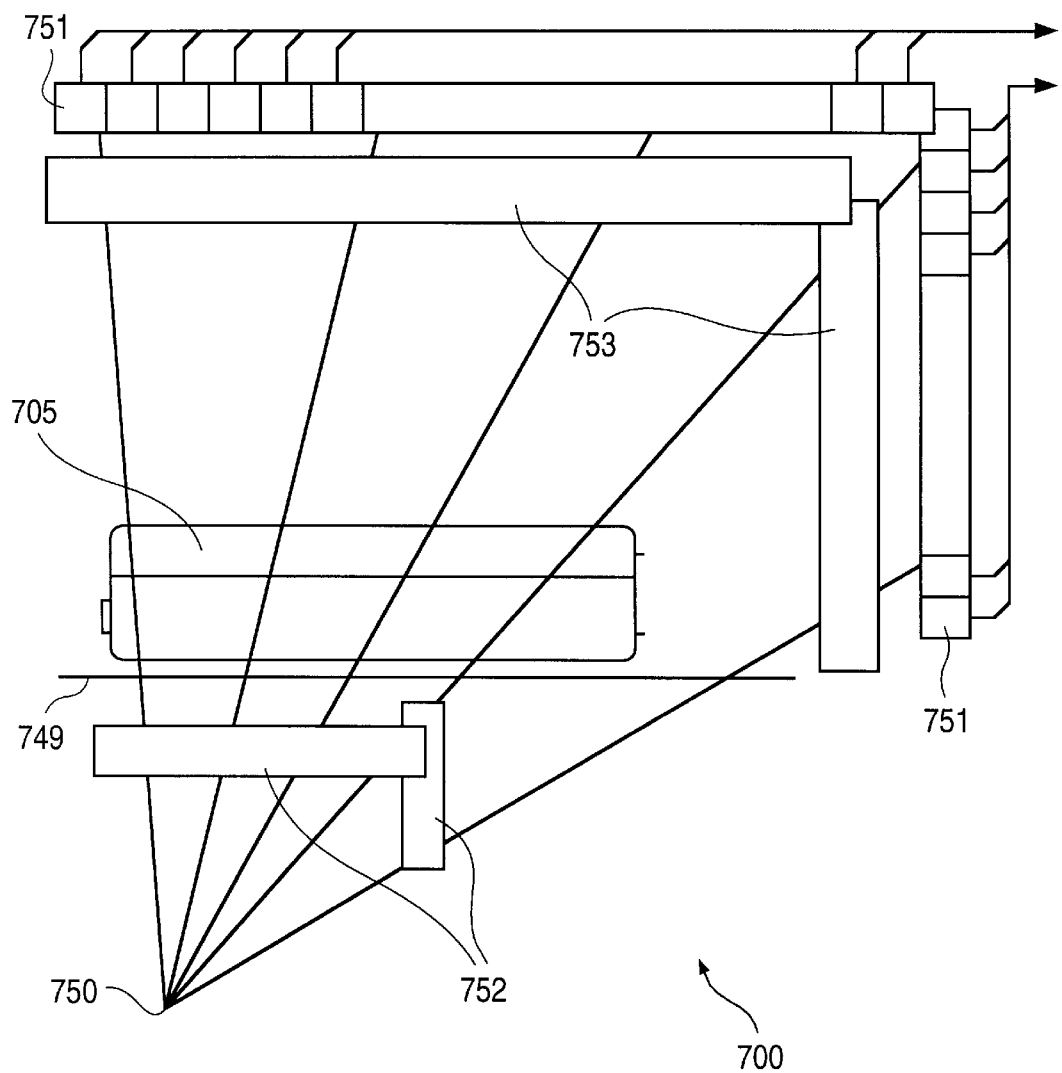

FIGS. 7A and 7B illustrate use of an embodiment of the invention in a luggage control facility 700. The luggage control facility includes a conveyor 749 which moves an analyzed object 705 (luggage) through an area between a penetrating radiation source 750 and a detector 751. X-ray radiation from source 750, which is under conveyor 749, passes through a collimator 752 forming many narrow, weakly diverging X-ray radiation beams. The beams further pass through object 705 to a spatial filter 753 that absorbs the non-scattered part of the radiation. The coherent radiation scattered at small angles passes through filter 753 and reaches detector 751. At each moment, detector 751 registers radiation deflected in a fragment of the internal structure of object 705. A processing unit 752, which is connected to detector 751 and a drive 755 for conveyor 749, records information from detector 751 concerning each fragment along with information about the position of object 705. From information indicating the fragment of the object's internal structure and the object's position, computing unit 754 generates a complete image of the object's internal structure and transfers the image to a video display 756. FIG. 7B shows relative positions of conveyor 749, radiation source 750, collimator 752, spatial filter 753, detector 751, and analyzed object 705. Alternative luggage control facility can employ other small-angle topography devices such as those shown in FIGS. 4, 5, or 6.

Figure 8:
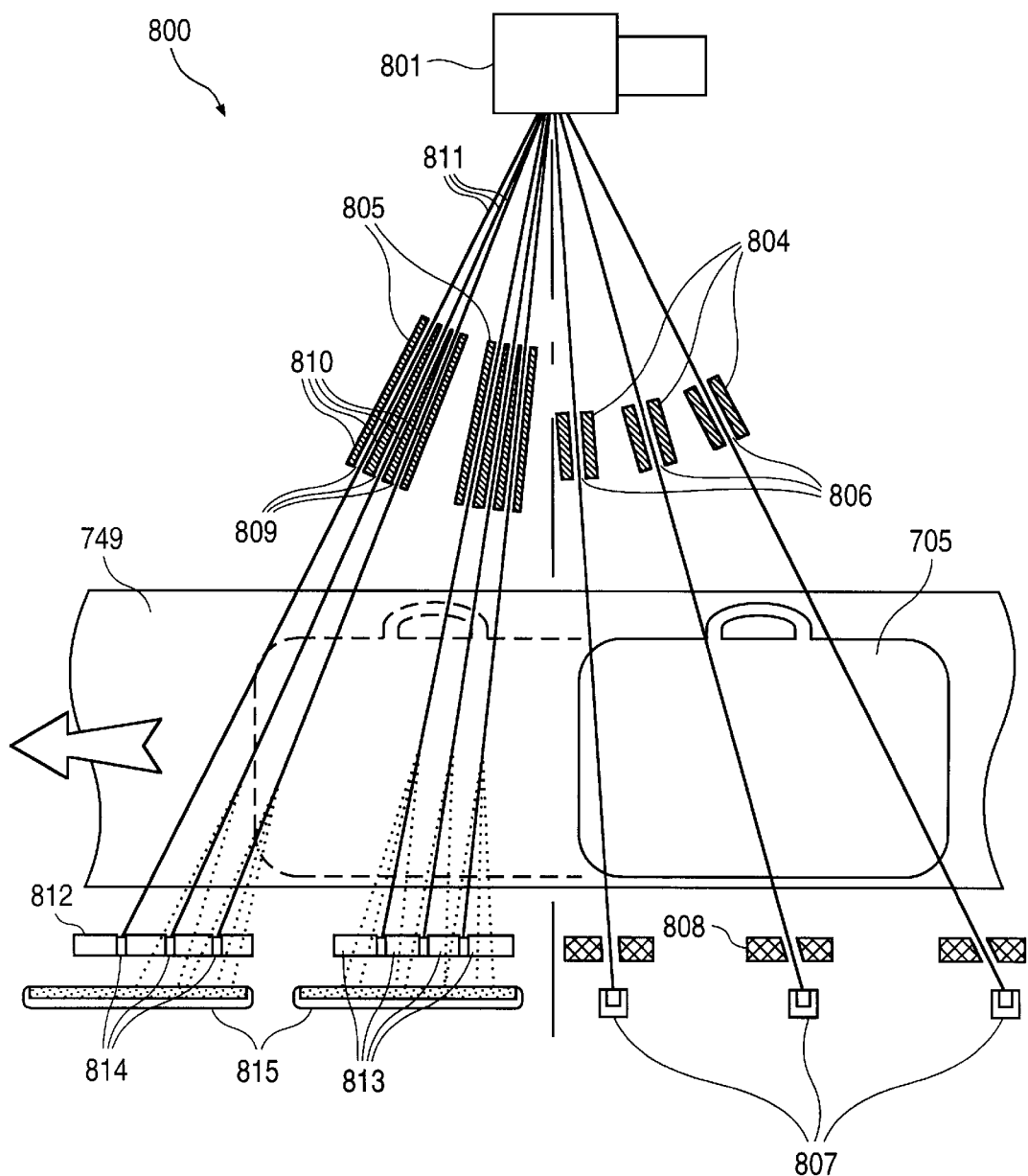
FIG. 8 shows a luggage control facility that in accordance with an aspect of the invention, separately measures radiation transmitted without scattering and radiation scattered at small angles.

In accordance with another embodiment of the invention, FIG. 8 shows a luggage control facility 800 including a transmission measurement system and an SAS measurement system. The transmission measurement system measures radiation transmitted without deflection through object (luggage) 705 and includes a source 801 of penetrating radiation, a collimator 804, a spatial filter 808, and coordinate sensitive detectors 807. The SAS measurement system measures radiation that object 705 deflects at small angles and includes of source 801, collimators 805, spatial filters 812, and coordinate-sensitive detectors 815. In the exemplary embodiment of the invention, source 801 is an X-ray tube that is common to both systems and directs radiation through collimators 804 and 805 to object 705 on moving conveyor 749. Conveyor 749 moves object 705 through the transmission measurement system and then through the small-angle measurement system.

Collimator 704 comprises separate blocks of material opaque to penetrating radiation, with slit-shaped transparent regions 806 formed in the blocks. Slit axes are along lines converging at a point coinciding with the focal spot of source 801 of the penetrating radiation (e.g., the X-ray tube focus). Beams from slits 806 are at angles with the plane of conveyor 749 that are as different as possible from each other. The slit widths select a beam size that preferably matches the widths of areas that sought substances are assumed to occupy in object 705. Perpendicular to the slit width, collimator 704 forms beams covering all of object 705. Coordinate-sensitive detectors 807 positioned parallel to collimator slits 806 record the radiation transmitted through object 705 without deflection. Each coordinate-sensitive detector 807 measures a series of radiation intensities corresponding to coordinates along a line parallel to slits 806. The coordinate resolution of each detector 807 determines the spatial resolution in the direction perpendicular to that of the object motion. A spatial filter 808 has a series of slits including a slit between each detector 807 and object 705. Filter 808 reduces the amount of deflected radiation reaching detectors 807 and thereby improves the signal-to-noise ratio for the recorded intensity of the transmitted radiation.

For SAS measurement, collimators 805 direct a number of narrow, weakly diverging beams to object 705. Each of collimators 805 has alternating opaque regions 810 and transparent regions 809 that form channels for the penetrating radiation. The axes of the channels in each of collimators 805 are along directions 811 converging at the focus of radiation source 801. The axes of the collimators 805 also converge at the source focus but are at various angles relative to conveyor 749. The orientations of central axes of collimators 805 are as different as possible from each other. Spatial filters 812 include transparent regions 813 and opaque regions 814 in the path of the radiation exiting object 705. Each spatial filter 812 is positioned relative to an associate collimator 805 so that opaque regions 814 of the filter block radiation from transparent regions 809 of the associated collimator 805. The radiation that object 705 scatters at small angles passes through transparent regions 813. The dimensions of the transparent regions (in this case, the widths and the depths of the slits), the structure period (distance between slits) of the collimators 805, and the dimensions of the transparent regions of spatial filters 812 are selected to ensure that associated coordinate-sensitive detectors 815 receive the radiation that object 705 scatters into a specific angular range. A typical angular range is from about 0 to 0.5 degrees but is preferably less that 6 to 12 angular minutes. Each detector 815 is a two-dimensional coordinate-sensitive element having resolution sufficient to build a small-angle scattering curve for each primary beam.

Figure 9:
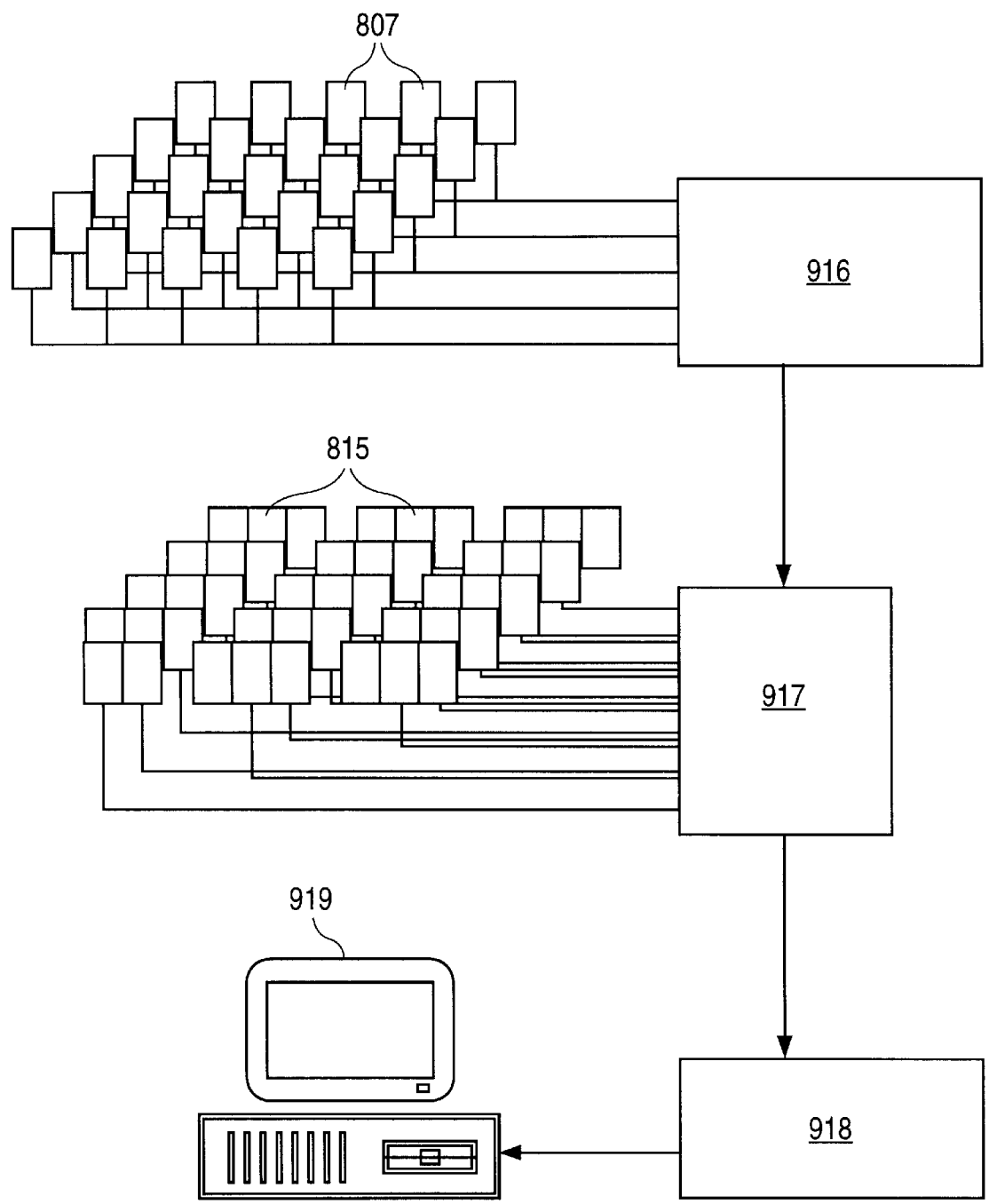
FIG. 9 illustrates data processing and output to a display screen for the system of FIG. 8.

Before object 705 reaches the transmission measurement system, detectors 807 measure the radiation intensities of the beams from collimators 804. A processing unit 916 shown in FIG. 9 receives from detectors 807 signals indicating unattenuated intensities. Processing unit 916 can be specialized hardware or a general purpose computer. While object 705 moves through the transmission measurement system, detectors 807 measure the intensity of radiation transmitted through object 705 at various angles, and processing system 916 receives signals indicating radiation intensities after partial absorption and scattering in object 705. Processing unit 916 calculates the ratios of the intensities measured in the presence of object 705 to intensities measured in the absence of object 705 and determines an absorption factor distribution over the volume of object 705.

For SAS measurements, filters 812 block direct radiation from reaching detectors 815. Accordingly, when object 705 is not in the small-angle measurement system, detectors 815 record only the background radiation intensity. An SAS data processing unit 917 shown in FIG. 9 receives and processes from the measured small-angle scattering intensity from detectors 815 and the absorption factor distribution from processing unit 916. Processing unit 917 compensates for absorption along the deflected paths when calculating small-angle scattering curves. Processing unit 917 processes the data obtained from the small-angle scattering systems. The small-angle scattering systems differ in the angles at which the primary beams traverse object 705 during scanning. This allows processing unit 917 to construct small-angle scattering curves for cells distributed over the volume of object 705. A processing unit 918 compares images of object 705 obtained for absorption and for small-angle scattering and compares the scattering curves for the cells in object 705 to a data base of small-angle scattering curves for known substances. Based on comparison results, a three-dimensional image of object 705 is formed and displayed on video display screen 919 with substances composing object 705 being identified.

Figure 10:
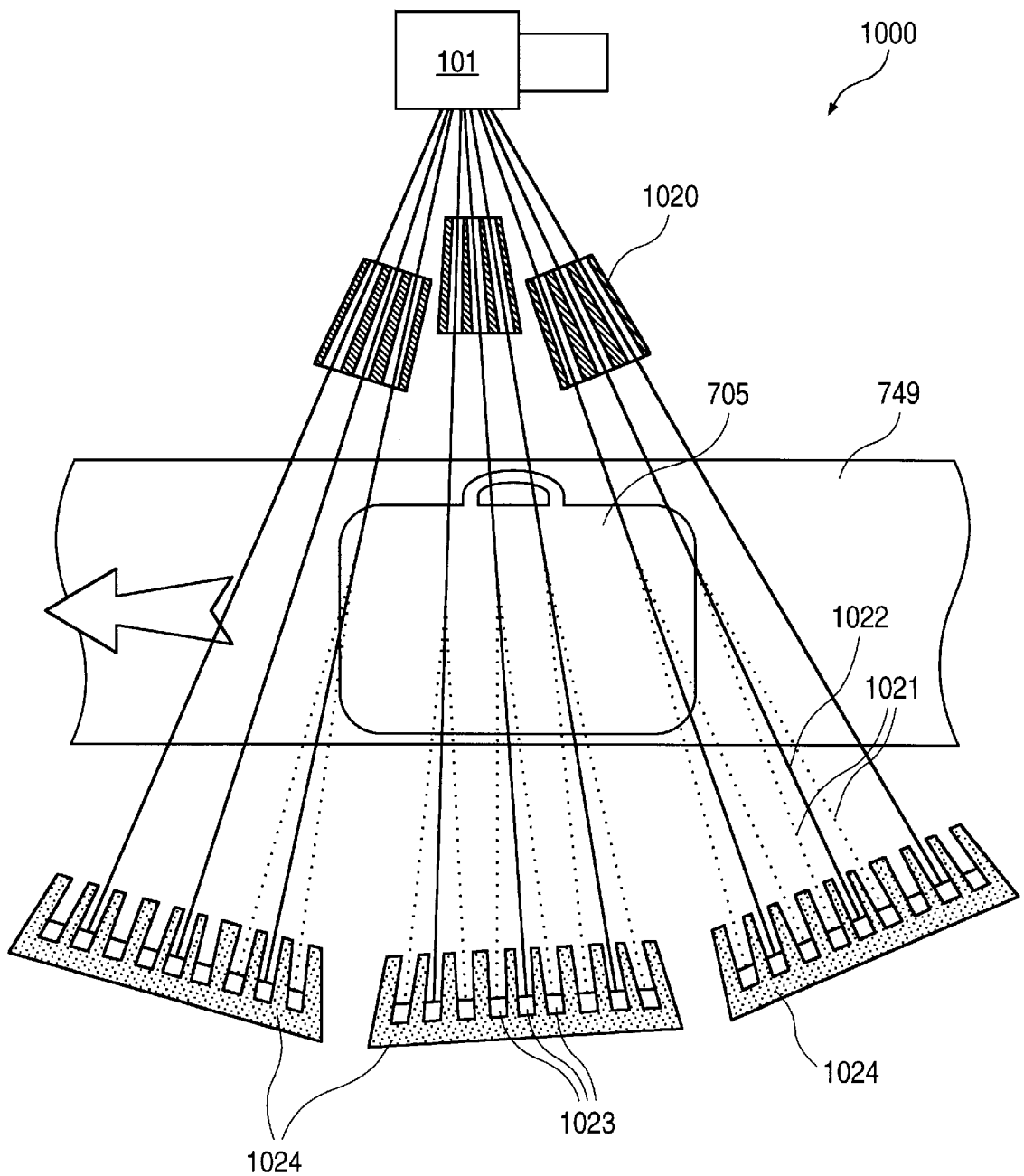
FIG. 10 shows another device embodiment of the invention in which the two detector system are combined in one spatial filter.

FIG. 10 shows an embodiment of a luggage control facility 1000 in accordance with the invention. Facility 1000 includes source 101 of penetrating radiation and collimators 1020 forming narrow weakly diverging fan-shaped beams. The fan-shaped beams are directed at object 705 which is on moving conveyor 749. Collimators 1020 are oriented with respect to object 705 so that their axes are inclined to the direction of motion of object 705 at angles that differ as much as possible from each other. Each collimator 1020 has a corresponding spatial filter 1024 and a corresponding set of coordinate sensitive detectors 1023. Coordinate-sensitive detectors 1023 are in slits in spatial filters 1024 and measure intensities of radiation 1021, which is scattered at small angles, and radiation 1022, which is transmitted without scattering. Each fan-beam from collimator is associated with at least two detectors 1023, a detector located along an undeflected path of the associated scan beam and a neighboring detector for measuring radiation scattered at small angles from the associated beam.

Figure 11:
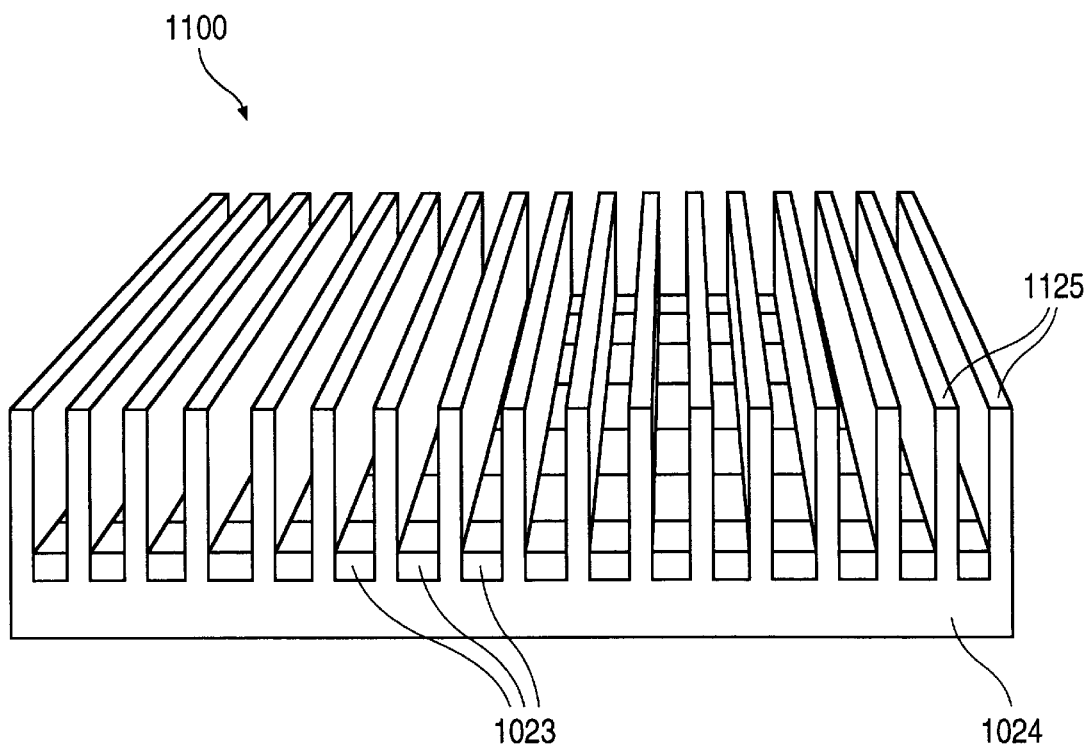
FIG. 11 shows a spatial filter and detector system which in accordance with an aspect of the invention is a slit raster with recording elements positioned in the slits.

FIG. 11 shows a perspective view of a filter and detector system 1100 associated with one of collimators 1020 in system 1000 of FIG. 10. System 1100 includes plates 1125 that are opaque to penetrating radiation and coordinate-sensitive detectors 1023 that are in the gaps between plates 1125. The thicknesses of plates 1125 are selected to prevent radiation scattered from one fan beam from reaching a detector 1023 associated with another fan-beam. The lengths and widths of the slots between plates 1125 are selected according to the requirement for each individual detector to record radiation falling in a specific angular range of transmitted or scattered radiation. Signals from detectors 1023 are transferred to processing units, such as units 916 and 917 of FIG. 9, via two independent channels. A first channel is connected to the detectors 1023 that record radiation intensities of undeflected radiation and carries data indicating absorption factors of materials composing the object. Detectors 1023 for absorption measurement can be linear coordinate-sensitive detectors that measure a series of intensities along the length of a slit. The second channel is connected to the detectors recording the radiation scattered at small angles. Detectors for measuring scattered radiation can be two-dimensional or linear coordinate-sensitive detectors. Two-dimensional coordinate-sensitive detectors can measure intensities at different angles relative to each point along a slit. A processing unit processes the two channels of information in the same fashion as described above and then transfers an image to a video display screen.

Although the invention has been described with reference to particular embodiments, the description is only an example of the invention's application and should not be taken as a limitation. Various adaptations and combinations of features of the embodiments disclosed are within the scope of the invention as defined by the following claims.

We claim:

1. A small-angle topography device comprising:
   a source of penetrating radiation;
   a collimator that forms scan beams from the penetrating radiation, the collimator being a regular periodic structure consisting of transparent regions alternating with the opaque regions;
   a facility for scanning an object through the scan beams to obtain a complete projection of the object;
   a spatial filter positioned behind the object, the spatial filter having a regular periodic structure complementary to that of the collimator so that regions of the spatial filter that correspond to the transparent regions of the collimator are opaque to the penetrating radiation the opaque regions of the spatial filter being disposed to block portions of the scan beams that pass through the object without deflection, transparent regions of the spatial filter being disposed to transmit portions of the scan beams that the object deflects at small angles;
   a coordinate-sensitive detector positioned to detect radiation that the spatial filter transmits during scanning; and
   a processing system that uses measurements from the coordinate-sensitive detector during the scanning, to determine a three-dimensional internal structure of the object.

2. The device of claim 1, wherein the collimator comprises a plate opaque to the penetrating radiation, in which transparent channels are made, with axes of the transparent channels converging at the focus of the radiation source.

3. The device of claim 2, wherein the spatial filter comprises a transparent plate, and the opaque regions comprise rods shaped regions of opaque material positioned in the transparent plate, to block penetrating radiation from the transparent channels in the collimator.

4. The device of claim 1, wherein the collimator comprises a set of plates with the gaps between the plates to form a system of slits that are the transparent regions of the collimator, the slits forming fan-shaped beams that are in planes that cross through a focus of the source.

5. The device of claim 1, wherein the transparent regions in the collimator are slit-shaped.

6. The device of claim 1, wherein the collimator comprises a set of polished plates that are stacked in contact with each other.

7. The device of claim 6, wherein one or more of the plates has an unpolished portion in an otherwise polished surface.

8. A small-angle topography device comprising:
   a source of penetrating radiation forming an incident radiation flux as a plurality of separated beams falling on an object to be analyzed;
   a spatial filter for the plurality of separate beams, the spatial filter including a plurality of plates behind the object; and
   a plurality of detector elements in slits formed between the plates.

9. The device of claim 8, further comprising a processing system coupled to receive data from the detector elements.

10. The device of claim 9, wherein the plurality of plates have orientations and dimensions that limit radiation reaching the detector elements to radiation that is scattered at small angles in the object.

11. The device of claim 8, wherein each detector element is smaller than one half of a projection of one of the beams on a plane containing the detector element.

12. The device of claim 8, wherein for each of the separate beams, the plurality of detector elements includes:
   a first detector element in an undeflected path of the beam; and
   a second detector element in a path of the beam that is deflected at a small angle in the object.

13. The device of claim 12, wherein for each of the separate beams, the plurality of plates have orientations and dimensions that limit radiation reaching the second detector element for the beam, to radiation that is scattered at small angles in the object.

14. The device of claim 12, further comprising a processing system, wherein processing system is coupled to receive data from the detector elements, and the processing system determines an absorption distribution from data received from the first detector elements for the beams and a distribution of small angle scattering from data received from the second detector elements for the beams.

15. A device for determining composition and internal structure of an object, comprising:

a source of penetrating radiation;

a collimation system that shapes radiation flux from the source and directs radiation toward the object;

a scanning system for moving the object relative to the source;

a first detector system that measures undeflected radiation transmitted through the object and identifies a distribution of absorption factor of the object; and a second detector system that measures radiation scattered at small angles, under 1°, in the object and identifies a plurality of scattering curves for the object.

16. The device of claim 15, wherein the collimation system comprises:

a first set of collimators that forms a first set of primary beams of radiation from the source, the first set of primary beams being directed toward the first detector system; and a second set of collimators that forms a second set of primary beams of radiation from the source, the second set of primary beams being directed toward the second detector system.

17. The device of claim 16, wherein each primary beam in the first set is a flat fan-shaped beam of radiation from the source.

18. The device of claim 16, wherein:

the second set of collimators comprises a plurality of multislit collimators;

each of the multislit collimators forms a number of flat weakly diverging fan-shaped beams of radiation from the source; and each of the multislit collimators has a central axis oriented at a different angle relative motion of the object.

19. The device of claim 16, further comprising a processing system coupled to receive data from the second detector system, wherein the processing system determines a scattering curve for each of the primary beams and compares each scattering curve to a data base of known scattering curves to identify composition of the object in a region through which the primary beam passes.

20. The device of claim 19, wherein the processing system is coupled to receive data from the first detector system and determines a three-dimensional distribution of absorption factors from data from the first detector system.

21. The device of claim 20, wherein the processing system when determining a scattering curve uses the distribution of absorption factors to compensate for effects of absorption.

22. A device for determining composition and internal structure of an object, comprising:

a source of penetrating radiation;

a collimation system that shapes radiation flux from the source and directs radiation toward the object;

a scanning system for moving the object relative to the source;

a first detector system that measures undeflected radiation transmitted through the object and identifies a distribution of absorption factor of the object; and a second detector system that measures radiation scattered at small angles in the object and identifies a plurality of scattering curves for the object, wherein the second detector system comprises a two-dimensional coordinate sensitive detector and a spatial filter positioned between the detector and the object, the spatial filter having opaque regions positioned to block radiation transmitted through the object without deflection and transparent regions positioned to transmit to the detector radiation that the object deflects at small angles.

23. A device for determining composition and internal structure of an object, comprising:

a source of penetrating radiation;

a unit for shaping a radiation flux directed to the object;

a plurality of plates that form slits behind the object;

a first plurality of detector elements positioned in the slits between the plates to record radiation transmitted undeflected through the object; and a second plurality of detector elements positioned in the slits between the plates to record radiation scattered at small angles in the object wherein the plurality of plates prevent undeflected radiation from reaching the second plurality of detector elements; and a processing system coupled to the first and second pluralities of detector elements, wherein the processing system forms an image of the object based on measurements of recorded radiation transmitted undeflected through the object and scattered at small angles in the object.

24. The device of claim 23, wherein each detector element comprises a set of recording elements arranged along a length of a slit containing the detector element.

25. The device of claim 23, wherein the processing system discriminates the radiation scattered at small angles from radiation transmitted through the object without scattering, and determines a scattering curve for a portion of the object.

26. The device of claim 25, wherein the processing system identifies a substance in the portion of the object by comparing the scattering curve to a data base of scattering curves for known substances.

27. The device of claim 23, wherein the unit for shaping the radiation flux forms a plurality of beams directed at the object, and a width of each detector element is smaller than half of a projection of a corresponding one of the beams onto a plane containing the detector element.

28. The device of claim 23, wherein the unit forming the flux in the direction of the analyzed object comprises a series of multislit collimators each of which is designed to form a number of flat weakly diverging fan-shaped beams from the single radiation source, the collimators being oriented so that their axes differ as much as possible different from each other.

29. The device of claim 23, further comprising a scanning system for moving the object with respect to the source.

30. The device of claim 23, wherein the small angles are less than 1°.

31. The device of claim 23, wherein the processing system determines a three-dimensional internal structure of the object.

* * * * *